United States Patent [19]

Rice et al.

[11] Patent Number: 4,906,100
[45] Date of Patent: Mar. 6, 1990

[54] METHOD OF DETECTING ADRIAMYCIN (DOXORUBICIN) OR DAUNOMYCIN IN THE ENVIRONMENT

[75] Inventors: Carol H. Rice, Cincinnati, Ohio; John Van Raalte, Portland, Oreg.; C. Eugene Moss, Cincinnati, Ohio

[73] Assignee: University of Cincinnati, Cincinnati, Ohio

[21] Appl. No.: 193,891

[22] Filed: May 13, 1988

[51] Int. Cl.[4] .............................................. G01N 21/64
[52] U.S. Cl. .................................. 356/417; 250/459.1
[58] Field of Search ....................... 356/317, 318, 417; 250/458.1, 459.1

[56] References Cited

U.S. PATENT DOCUMENTS

| 4,170,987 | 10/1979 | Anselmo et al. | 128/665 |
|---|---|---|---|
| 4,178,917 | 12/1979 | Shapiro | 128/665 |
| 4,200,801 | 4/1980 | Schuresko | 250/458.1 |
| 4,267,844 | 5/1981 | Yamanishi | 128/633 |
| 4,283,625 | 8/1981 | King | 128/633 |
| 4,290,433 | 9/1981 | Alfano | 128/665 |
| 4,336,809 | 6/1982 | Clark | 128/665 |
| 4,515,476 | 5/1985 | Ingmar | 250/458.1 |
| 4,528,986 | 7/1985 | Arundel et al. | 128/665 |
| 4,794,260 | 12/1988 | Asano et al. | 250/458.1 |

OTHER PUBLICATIONS

Gibson, H., Medical Photography, Eastman Kodak, Rochester, N.Y., pp. 123–130.
Tuan Vo-Dinh and Richard B. Gammage, Am. Ind. Hyg. Assoc. J. (42), Feb., 1981, pp. 112–120.
R. Kennan and S. B. Cole, Am. Ind. Hyg. Assoc. J. (43), Jul., 1982, pp. 473–476.
Ronald H. Hill, Am. Ind. Hyg. Assoc. J. (45) (7): 474–484 (1984).
Steven D. Reich, Cancer Nursing, 6:313–315, Aug., 1983.
Richard A. Fenske et al., Am. Ind. Hyg. Assoc. J. 47 (12): 764–770 (1986).
Richard A. Fenske et al., Am. Ind. Hyg. Assoc. J. 47 (12): 771–775 (1986).
Gibson, H., Medical Photography, Eastman Kodak, Rochester, N.Y., 1973, pp. 9–25.

Primary Examiner—Vincent P. McGraw
Attorney, Agent, or Firm—Wood, Herron & Evans

[57] ABSTRACT

A method of detecting anti-neoplastics particularly adriamycin by shining visible light through a filter at the anti-neoplastic. The filter effectively removes light which is not in the absorption spectrum of the anti-neoplastic. Light which is reflected off of the anti-neoplastic as well as fluorescing light is then permitted to pass through a second filter and into a detector. The second filter is designed to filter out any light emitted by the light source and permit basically only light that is fluorescing from the anti-neoplastic. The light passing through the filter is then detected by a detector. In one embodiment, the second filter is a pair of glasses and the detector is the eye of an individual. The light source can be portable providing a hand held light source to quickly scan the environment. This is effective in detecting extremely dilute concentrations of adrimycin.

7 Claims, 3 Drawing Sheets

Absorption spectrum of adriamycin HCl in sterile saline solution with lactose. 200-700nm background corrected.

Adriamycin emission spectrum excitation 470nm.

Adriamycin excitation spectrum, emission 580 nm.

Energy output of projector available to stimulate fluorescence.

METHOD OF DETECTING ADRIAMYCIN (DOXORUBICIN) OR DAUNOMYCIN IN THE ENVIRONMENT

BACKGROUND OF THE INVENTION

Modern anti-neoplastic drugs are highly toxic. Health care personnel who formulate, administer and clean surfaces that have contacted these drugs may be at risk of developing a number of adverse effects including cancer and fetal loss. By far the most commonly employed anti-neoplast is adriamycin (doxorubicin). This a member of a class of drugs which have the anthracycline structure. A second common anthracycline anti-neoplast is daunomycin also called daunorubicin.

Only two studies have been published reporting any environmental sampling of anti-neoplastics in the hospital setting. Both these papers reported airborne levels of anti-neoplastics though neither study developed methods for generalized use in airborne exposure assessment. Neal et al 1983 conducted air sampling for four drugs fluorocil, adriamycin, methotrexate and cyclophosphamide with teflon filters at drug mixing counters at three hospitals. Adriamycin was detected by fluorescence with an exitation at 239 nm and 550 emission cut off. The other three drugs were separated with high performance liquid chromatography and detected spectra photometrically.

The use of fluorescence as a sensitive and selective analytical tool is well established. It is one of a number of techniques which exploit the interaction of light, or more broadly electromagnetic radiation with matter.

When light comes into contact with matter it can be reflected, transmitted or absorbed. If it is absorbed, energy is transferred to the material whereupon two things can happen. The material either heats up or the light is re-emitted. In fluorescence or phosphorescence light of a particular wavelength is absorbed, then a certain portion of this energy is lost to enhance molecular vibration and finally the light is re-emitted at a longer wavelength.

The ability of the individual to perceive fluorescence is an important part of the detection process. Dark adaptation of the eye or scotopic vision requires approximately 20 minutes, at which time the eye will be most sensitive to light of lower intensities. For this reason, ultraviolet exitation of fluorescence is preferred for observation purposes. Since the ultraviolet light cannot be detected by the human eye it provides an ideal source of exitation light for fluorescence and subsequent detection, presuming the material studied in fact absorbs in the ultraviolet range. Adriamycin does in fact have an absorption peak from 200 to 300 nm falling well within the ultraviolet range.

Unfortunately, ultraviolet light is considered to have carcinogenic potential. When added to the potential carcinogenic substances already on the skin, the risk of carcinogenic effects may be increased. See Parrish et al 1978.

Several investigators have utilized ultraviolet stimulated fluorescence of adriamycin to detect its presence. Although the absorption spectrum of adriamycin includes bands both in the ultraviolet and visible spectrum neither per se is suitable for study. As indicated the ultraviolet light is believed to have carcinogenic potential. Further, the shining of a light in the visible range will have a masking effect reducing the effectiveness in detection of minute amounts of adriamycin. Further this will have particular negative effects in quantitative evaluation of adriamycin present in the environment.

SUMMARY OF THE INVENTION

The present invention is premised on the realization that one can effectively detect anthracycline anti-neoplastic drugs by shining light in the visible spectrum at the anthracycline and subsequently detecting the fluorescence either visually or with other light detection sources such as a camera. More particularly, the present invention is premised on the realization that by shining light onto these drugs particularly adriamycin wherein the emission spectrum of the light has a portion which lies between 400 and 560 nm preferably around 470 nm but no light exceeding 560 nm. Light emanating from the area is filtered before passing into the detector. The filter removes all light having a wavelength less than about 550 nm. This effectively removes the light which interferes with visual detection of the fluorescence of the adriamycin which predominantly occurs between 550 and 600 nm.

More particularly, the present invention is premised on the realization that one can shine a light through a first filter filtering out most of the emitted light. However, the filter allows a narrow band of light, at least a portion of which is between about 450 and 510 nm to pass through. This is shined onto an area being studied. When it strikes an anthracycline anti-neoplast it will both reflect off the surface and cause the anthracycline to fluoresce at about 550–600 nm. Both the fluorescing and reflected light (collectively referred to as the remitted light) pass through a filter which filters out any light which is less than 550 nm. The filter may be a pair of glasses and the detector the human eye. This permits only the fluorescing light to pass through the filter to be detected by the detector source and is provides a very effective method of detecting adriamycin. When used in combination with a camera as the detecting source, the concentration of adriamycin can be quanified.

The invention will be further appreciated in light of the following detailed description and drawings in which:

DETAILED DESCRIPTION OF THE INVENTION

Figure 1:
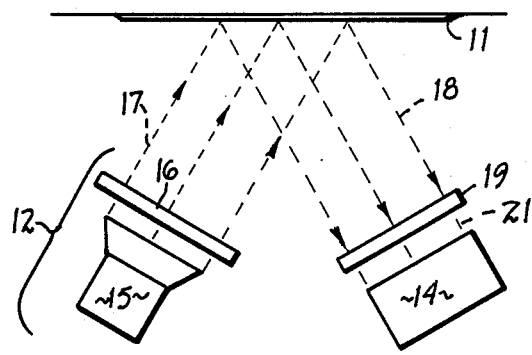
FIG. 1 is a diagrammatic view of the present invention.

The present invention is a method of detecting anthracycline anti-neoplastic drugs in the environment. The primary anthracyclines are adriamycin (doxorobin) and daunomycin (daunorubicin). This can be either on an individual's skin or on a work surface for example in a hospital environment or a pharmacy. As shown in FIG. 1, the anthracycline anti-neoplastic 11 is detected using a light source 12 and a detector 14. The light source includes a combination light 15 and filter 16 which emits rays of light 17 which has an emission spectrum. The emission spectrum must be such that it at least in part overlaps the visible absorption spectrum of anthracycline anti-neoplastic.

Figure 3:
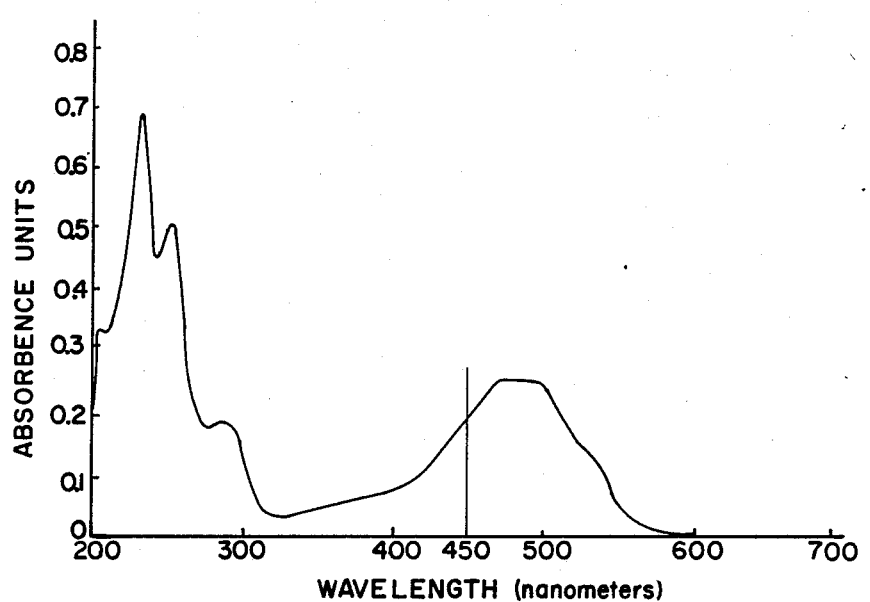
FIG. 3 is a diagram of the absorption spectrum of adriamycin HCl.

As shown in FIG. 3, the absorption spectrum of adriamycin in the visible range extends from about 400 nm to about 560 nm but is highest around between 450 to 510 nm with the peak being between 470 and 500 nm. This is a characteristic of anthracyclines.

The emission spectrum of light 17 should not include any portion which exceeds about 560 nm and preferably has no light which exceeds 510 nm. Even more preferably it should not have any light which exceeds 500 nm. A light source which emits light only at about 470 nm is ideal.

This can be accomplished in one of two ways. The light source 15 can per se have an emission spectrum that emits between 400 and 510 nm but has no portion which is greater than 510 nm. Alternately, if the light source has a portion which exceeds 510 nm a filter can be employed to remove all light exceeding 510 nm. Such selective filters are readily available. The light shining on the anthracycline anti-neoplastic 11 will cause a re-emitted light 18 to reflect off of the adriamycin and be detected by anthracycline anti-neoplastic detector 14. This re-emitted light includes any light which is included in the emission spectrum of light being 17 which is not absorbed by the anthracycline anti-neoplastic as well as any fluorescing light emitted by the anthracycline anti-neoplastic.

Figure 4:
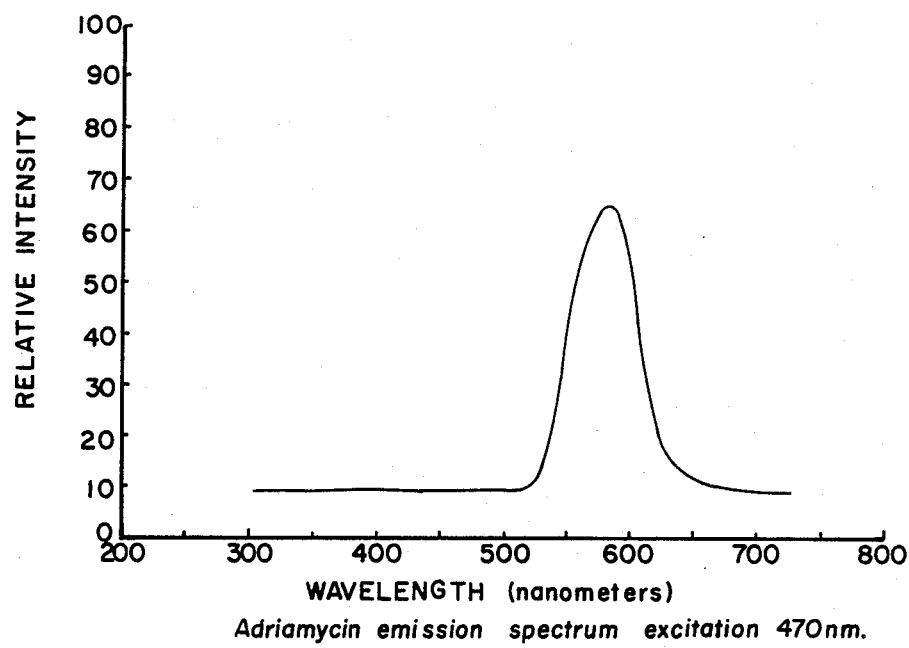
FIG. 4 is a diagram of the adriamycin emission spectrum exitation at 470 nm.

Only the fluorescing light should be detected. Accordingly, the detector 14 includes a filter 19 which effectively filters out any light which has a wavelength lower than the emission spectrum of the anthracycline anti-neoplastic. The emission spectrum of adriamycin is shown in FIG. 4. Again this characteristic of anthracyclines. It extends from 525 to 625 nm but is readily detectable at 550 to 600 nm and peaks at about 580. Accordingly, the filter must filter out any light below 525 and preferably blocks out any light less than 550 nm. It would be effective if it filtered out any light less than 580 nm. Again, such filters are readily available and can be purchased. Light 21 which then passes through filter 19 should be primarily caused by fluorescence of anthracycline anti-neoplastic. Detecting this light in effect detects the anthracycline anti-neoplastic present.

Figure 2:
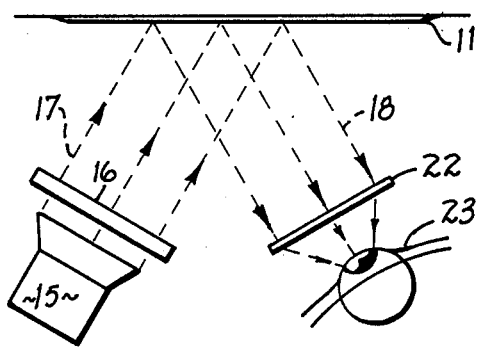
FIG. 2 is a diagrammatic view of an alternate embodiment of the present invention.

The detector can be any light detector. To quantitatively evaluate the anthracycline anti-neoplastic present a camera or photometer can be employed as detector 14. However, as shown in FIG. 2 the human eye can act as the detector.

In this embodiment, the light source 15 and filter 16 remain the same emitting the same light having the same emission spectrum 17 onto the anthracycline anti-neoplastic 11. This in turn re-emits light 18 which includes reflected light and fluorescing light from the anthracycline anti-neoplastic. A filter 22 is employed to filter out light observed by the eye 23. In this embodiment, however, the filter will be a pair of filtering glasses similar to sunglasses which will effectively block out light less than 500 nm and preferably anything less than about 550 nm.

Thus, by employing the filters of the present invention one can detect anthracycline anti-neoplastic in the workplace. The surfaces studied could include human skin, floors, waste cans and receptacles, work benches, hoods, clothing, lab jackets, virtually any surface which may come into contact with the adriamycin. Preferably, the light source 15 will be a hand held light source emitting at least about 300 kilowatts of light. The invention will be further appreciated in light of the following example.

EXAMPLE

Adriamycin hydrochloride (Adria Laboratories, Columbus, Ohio Lot A1426 expiration date 4/88) was reconstituted to clinical strength. The fresh solution was diluted to $1.72 \times 10^{-5}$ molar with sterile saline (0.9% sodium chloride for injection, Lot 78-520DK expiration 7/1/87 Abbott Laboratories, North Chicago). This solution contained $8.60 \times 10^{-5}$ molar lactose. The UV-visible absorbent spectrum was obtained between 200 and 700 nm using a Perkins Elmer Model 552 Spectrophotometer (band pass—4 nm; scan speed—120 nm per minute; response time—0.5/sec.) and 1.0 cm match quartz cells. Background corrected spectrum is shown in FIG. 3. Absorption in the visible spectrum with a peak between 460 and 500 nm is evident along with the primary absorption and the short wavelength ultraviolet region.

A preliminary exitation/emission spectrum for adriamycin hydrochloride in saline solution was then obtained using a spectrofluorometer (Aminco-Bowman Model 768-H) which lacked a background corrector. The emission spectrum is provided as FIG. 4. Under the conditions, the fluorescence extends from 525 nm to 650 nm with the maximum occurring at 580 nm.

Figure 5:
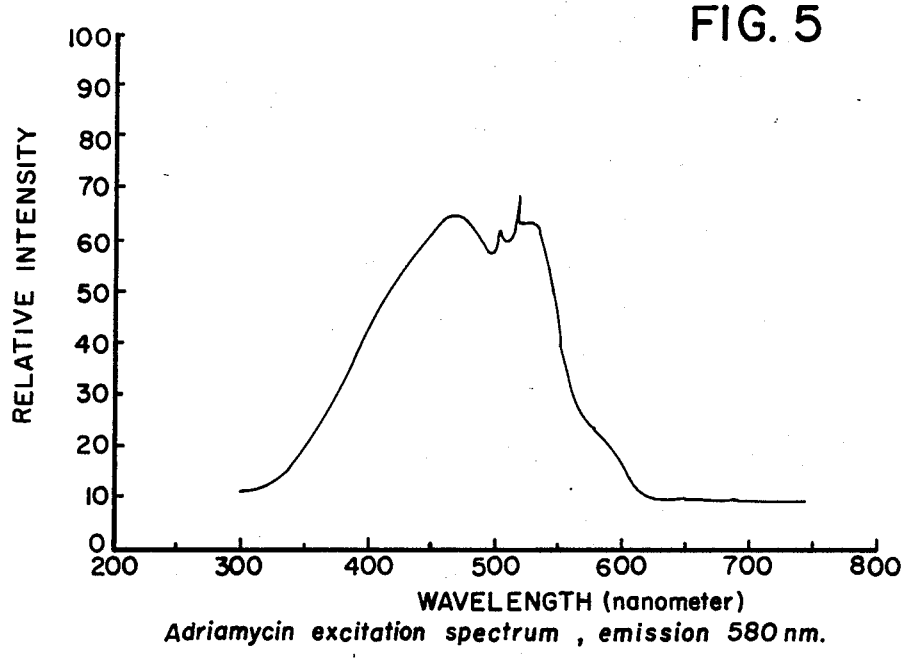
FIG. 5 is a diagram of the adriamycin exitation spectrum at 580 nm.

Monitoring the fluorescence at 580 nm the exitation wavelength was varied to produce the exitation spectrum as shown in FIG. 5. The maximum intensity at 580 nm was produced by exitation at 470 nm as expected.

To detect samples under ambient conditions a Kodak Model AF-1 Ektographic Slide Projector was used as a light source to stimulate fluorescence. The optical system of the projector was equipped with a condensing lens and an infrared filter (Kodak Corp., Rochester, NY). This projector was fitted with a new General Electric ELH Multimirror 300 Watt 120 Volt Tunsten Halogen Projection Lamp of 3350 Kelvin Color temperature (General Electric Co., Cleveland, OH). A glass filter, Model BG-124084 which selectively passed short wave (blue) visible light was passed in the slide projector compartment. This filter is designed to fit into the slide projector. The spectral transmission of the Model BG-124084 filter is shown in FIG. 6.

A Minolta SRT201 35mm single lens reflex camera with a Vivatar 55mm 1:2.8 macro lens and Kodak Wratten No. 21 75×75mm gelatin filter was used to photograph the fluorescent emission from adriamycin. This gelatin filter required the use of a Kodak 75×75 gelatin filter frame and series 8 75×75mm gelatin filter frame holder and Tiffon Model 62M-M 62mm adapter ring. The lens mounted Wratten filter absorbed the stimulating blue light emitted by the light source allowing only the orange red fluorescent glow of the adriamycin to be photographed. Viewing spectacles were worn over the eyes during visual observation to filter out the interfering light emitted by the stimulating light source. Ultraviolet and blue filtering sunglasses manufactured by Sun Tiger, Pasadena, CA blocked transmission of light below 550 nm and were used in this research.

Figure 6:
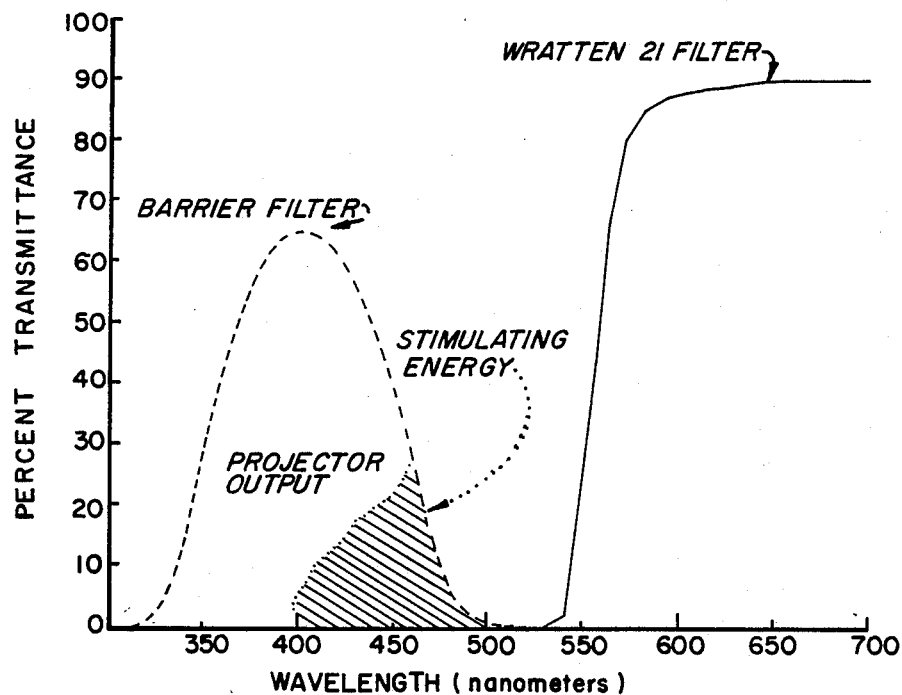
FIG. 6 is a diagram showing energy output of a projector of example 1, overlapping absorption spectrum of adriamycin and effective detector filter wavelength.

The spectral transmission curves of the Wratten No. 21 filter and the viewing spectacles is also shown in FIG. 6. These results were obtained on a Perkin Elmer Model 330 Spectrophotometer.

The light output of the projector available to stimulate fluorescence is plotted by combining the spectral irradiance plot of the projector with the spectral transmission curve of the BG-12 filter as shown in FIG. 6.

The use of photography to report fluorescence involved several parameters which were systematically varied to optimize the method. Aperture setting, exposure time, angles and distances between the camera, light source and subject and film were each varied while the other four were held constant. Slides were made and viewed to determine optimum parameters.

Several different types of film were used. Initially Kodacolor VR 1000 and 400 print film was used with Kodak processing although fluorescence was easily visible on the print these daylight films did not give good results even with optimization of exposure time and aperture setting. Kodak Ektochrome 160 tungsten slide film was chosen for the remainder of the study due to its availability and relatively low cost.

The relatively slow Ektochrome tungsten 160 ASA film required 1 to ⅛ second exposure times and an F stop of 2.8. This widest aperture setting was used for all photography to minimize exposure time. Push processing the film to speeds of ASA 320 with corresponding shorter exposure times could be used if necessary. This was not deemed necessary. A faster film such as 3M 640 could also be used to reduce exposure time. Except for initial unsatisfactory prints mentioned above all film processing was done by Robin Color Labs, Cincinnati, Ohio.

At 25 cm from the lens with the beam focused as tightly as possible and the blue filter in the beam the illuminance was 405 Lux measured with a Lite Mate Model 501 Photometer. At 25 cm without the filter the projector illuminance was 90,000 Lux. The adriamycin samples were photographed in the laboratory at approximately 25 cm from the projector light source and approximately 20 cm from the camera.

The background luminance of the various subject materials varied widely. Measured at 25 cm with the projector providing illuminance through the blue BG-124084 filter, white cloth had a luminance of 45 footlamberts, bench top absorbent padding 28 foot-lamberts, latex glove material 26 foot-lamberts and stainless steel 3.5 foot-lamberts. These values were obtained with a Spectra Minispot Meter. Photos and visual observations through filters which cut blue light such as the Wratten No. 21 and viewing spectacles reduced these values further.

Ambient light levels during laboratory photography were always less than 10 Lux as measured with the Lite Mate. To insure constant intensity and maximize sensitivity the angle between the projected and emitted light beams should be as small as possible; in this research it was held to 45° or less.

In order to observe a range of fluorescence various dilutions were formulated. Adriamycin hydrochloride in sterile saline solution was diluted with sterile saline to produce 9 standard concentrations: 2 mg/ml, 1 mg/ml, 0.5 mg/ml, 0.1 mg/ml, 0.05 mg/ml, 0.025 mg/ml, 0.01 mg/ml, 0.005 mg/ml and 0.001 mg/ml. The weakest concentrations were used to simulate the residues which might remain on surfaces after efforts to clean up a spill.

Initially, 20 microliters of each concentration was placed on each of four sample materials: stainless steel, strips of 65% polyester/35% cotton lab coat cloth, pieces of material cut from latex examination gloves and strips of disposable laboratory bench top absorbing padding. These were all photographed after two hours of drying time. Visual detection of adriamycin fluorescence was easily accomplished using a slide projector as a light source for fluorescence stimulation in the viewing spectacles. Adriamycin contamination undetectable to the naked eye in normal room lighting conditions was observed with background light levels ranging from 10 Lux to 35 Lux. Red orange fluorescence was observed on all test materials at all concentrations except for the most dilute 0.001 mg/ml which was not observed to fluoresce on stainless steel or latex. This dilute solution did fluoresce on cloth and absorbent padding.

With background light levels under 10 Lux, photographs were taken demonstrating adriamycin fluorescence on test materials. All these photographs were taken with the stimulating light source and camera held at 20–25 cm from the fluorescent material and the angle between the light source and camera held to less than 45°.

To observe the linear range of fluorescence quantitatively a section of filter paper was soaked in each of the nine standard solutions and allowed to dry thoroughly. Sections were examined in a dark room under stimulation with a projector and filter of 25 cm. A Spectra Pritchard Photometer was used to detect fluorescent light held at a distance of 30 cm from the samples as illuminated by the projector spaced at 25 cm. The results of the Pritchard photometer measured at a distance of 15 cm with a 20 minute field of view are depicted in Table 1.

TABLE 1

| | Pritchard Photometer Results | | |
|---|---|---|---|
| Concentration (mg/ml) | Column A Flourescence luminance (with Wratten filter) (ft-lamberts) | Column B Total luminance (without Wratten filter) (ft-lamberts) | Column C Contribution of fluorescence (flurorescence intensity as percentage of total luminance) |
| 0.001 | 0.10 | 14.60 | 0.7 |
| 0.005 | 0.25 | 14.02 | 1.8 |
| 0.01 | 0.29 | 14.80 | 2.0 |
| 0.025 | 0.52 | 14.60 | 3.6 |
| 0.05 | 1.22 | 13.96 | 8.7 |
| 0.1 | 1.46 | 12.54 | 11.6 |
| 0.5 | 1.53 | 9.40 | 16.3 |
| 1.0 | 1.12 | 6.60 | 16.7 |
| 2.0 | 0.98 | 5.2 | 18.9 |

Fluorescence luminance (Col. A) with the Wratten filter eliminating interfering light increases with increasing concentration up to an adriamycin concentration of 0.5 mg/ml. Luminance decreases with higher concentrations. This effect is probably due to concentration quenching. As concentration increases over three orders of magnitude luminance increases over one order of magnitude. The most dilute solutions emit measurable fluorescence but its low value 0.1 foot-lamberts indicates why fluorescence detection is sensitive to interfering light in the survey area.

Without the Wratten filter to eliminate interfering light (Col. B) the total luminance of the paper decreases with increasing adriamycin concentration. This is due to the overwhelming contribution of the interfering light to the total signal and the increasingly dark red color of the adriamycin deposits. As the concentration increases, more and more incident light is absorbed as color deepens. The relative contribution of fluorescence (Col. C) has a correlation coefficient of 0.97 with a concentration over the range of the nine standards and appears to be especially well correlated over the range of 0.5 mg/ml to 0.005 mg/ml.

Densitometry was also performed on photographs of adriamycin fluorescence taken with the Wratten filter eliminating interfering light. Stainless steel and cloth rather than filter paper were used as representative carriers for the adriamycin. After drying the adriamycin coating on steel was not uniform and photography was not attempted of the stainless steel samples. Of the cloth samples, the photographs of fluorescence were taken under standard conditions and the negative examined for optical density with a densitometer. Each negative was measured in the four corners of the luminous fluorescent field and in the center of the field. The five results were averaged to get an overall optical density for the fluorescent field given by the equation $$\text{Optical density} = \text{LOG}_{10} \frac{\text{Light In}}{\text{Light Out}}$$

The results of the densitometry on photographs of adriamycin fluorescence cloth are shown in Table 2 and these correspond relatively to the results of Table 1.

TABLE 2

Results of Densitometry on Photographs of Adriamycin Fluorescence on Cloth

| Concentration (mg/ml) | Average Optical Density (logarithmic) |
|---|---|
| 0.001 | 1.418 |
| 0.005 | 1.476 |
| 0.01 | 1.498 |
| 0.025 | 1.512 |
| 0.05 | 1.515 |
| 0.1 | 1.505 |
| 0.5 | 1.404 |
| 1.0 | 1.345 |
| 2.0 | 1.352 |

Thus, by using the method of the present invention one can accurately determine the presence of adriamycin in the environment either on skin or on any item in a laboratory or clinical setting. The present method provides both a very rapid qualitative evaluation of the presence of adriamycin using a hand held projector emitting visible light and sunglasses detecting the fluorescence using eyesight or alternately a quantitative method using a camera as the light fluorescence detector or else using a photometer as the fluorescence detector both in combination with an appropriate filter.

The preceding has been a description of the preferred embodiment of the present invention.

However, we intend to be bound only by the claims wherein we claim:

1. A method of detecting anti-neoplasts in the environment comprising shining light having an emission spectrum at said anti-neoplast
    wherein at least a portion of said emission spectrum is visible light having a wavelength less than 550 nm and wherein said emission spectrum does not include a portion of light having a wavelength in excess of 550 nm;
    detecting fluorescent light emitted from said anti-neoplast by filtering re-emitted light from said anti-neoplast permitting only light having a wavelength greater than about 550 nm to pass into detector;
    detecting the light passing into said detector.

2. The method claimed in claim 1 wherein said light having said emission spectrum is shined onto said anti-neoplast by passing a light source having a broad emission spectrum through a second filter to establish said first emission spectrum wherein said filter removes substantially all of said light having a wavelength greater than 550 nm.

3. The method claim in claim 2 wherein said second filter filters all light having a wavelength greater than about 500 nm.

4. The method claimed in claim 1 wherein said anti-neoplast is an anthracyclene.

5. The method claimed in claim 4 wherein said anthracyclene is selected from the group consisting of doxorobin and daunorubicin.

6. The method claimed in claim 2 wherein said detector is a human eye and said filter is a pair of glasses.

7. A method of detecting anti-neoplast in the environment comprising shining light having an admission spectrum at said neoplast;
    wherein at least a portion of said admission spectrum is visible light having a wavelength less than 550 nm and wherein said admission spectrum does not include a portion of light having a wavelength in excess of 550 nm
    detecting fluorescent light emitted from said anti-neoplast by the human eye by filtering readmitted light from said anti-neoplast with a pair of glasses wherein said pair of glasses permits only light having a wavelength greater than 500 nm to pass into said human eye.

* * * * *